United States Patent
Holmes et al.

(10) Patent No.: US 10,891,748 B2
(45) Date of Patent: Jan. 12, 2021

(54) PROCESSING OPTICAL COHERENCE TOMOGRAPHY SCANS

(71) Applicant: Michelson Diagnostics Ltd., Maidstone (GB)

(72) Inventors: Jonathan D. Holmes, West Malling (GB); Richard Whitehead, Lingfield (GB)

(73) Assignee: Michelson Diagnostics Ltd., Maidstone (GB)

( * ) Notice: Subject to any disclaimer, the term of this patent is extended or adjusted under 35 U.S.C. 154(b) by 0 days.

(21) Appl. No.: 15/549,850

(22) PCT Filed: Feb. 17, 2016

(86) PCT No.: PCT/GB2016/050395
§ 371 (c)(1),
(2) Date: Aug. 9, 2017

(87) PCT Pub. No.: WO2016/135454
PCT Pub. Date: Sep. 1, 2016

(65) Prior Publication Data
US 2018/0018785 A1 Jan. 18, 2018

(30) Foreign Application Priority Data
Feb. 26, 2015 (GB) .................... 1503196.6

(51) Int. Cl.
*G06K 9/00* (2006.01)
*G06T 7/55* (2017.01)
(Continued)

(52) U.S. Cl.
CPC .............. *G06T 7/55* (2017.01); *A61B 5/0073* (2013.01); *A61B 5/445* (2013.01); *G06T 7/0016* (2013.01);
(Continued)

(58) Field of Classification Search
CPC ................. G06T 7/55; G06T 7/0016; G06T 2207/30088; G06T 2207/10101; G06T 2207/30104; A61B 5/445; A61B 5/0073
(Continued)

(56) References Cited

U.S. PATENT DOCUMENTS

2014/0073917 A1 3/2014 Huang et al.
2014/0268167 A1* 9/2014 Friedman .................. G01J 9/02
356/479
(Continued)

FOREIGN PATENT DOCUMENTS

EP 2763103 A2 8/2014
EP 2829219 A1 1/2015
(Continued)

OTHER PUBLICATIONS

Liew, Yih Miin, et al. "In vivo assessment of human burn scars through automated quantification of vascularity using optical coherence tomography." Journal of biomedical optics18.6 (2012): 061213. (Year: 2012).*

(Continued)

*Primary Examiner* — Andrew M Moyer
(74) *Attorney, Agent, or Firm* — Burns & Levinson LLP; Steven M. Mills

(57) ABSTRACT

A method of processing optical coherence tomography (OCT) scans through a subject's skin, the method comprising: receiving a plurality of scans through the subject's skin, the scans representing an OCT signal in slices through the user's skin at different times; comparing the scans to determine time-varying regions in the scans; determining a depth-distribution of the time varying regions.

17 Claims, 3 Drawing Sheets

(51) Int. Cl.
*G06T 7/00* (2017.01)
*A61B 5/00* (2006.01)

(52) U.S. Cl.
CPC ........... *G06T 2207/10101* (2013.01); *G06T 2207/30088* (2013.01); *G06T 2207/30104* (2013.01)

(58) Field of Classification Search
USPC ....................................................... 382/131
See application file for complete search history.

(56) References Cited

U.S. PATENT DOCUMENTS

| | | | | |
|---|---|---|---|---|
| 2015/0080742 | A1* | 3/2015 | Andre | A61B 5/0059 600/477 |
| 2016/0228000 | A1* | 8/2016 | Spaide | G06T 15/08 |
| 2018/0218506 | A1* | 8/2018 | Carolus | G06T 7/0012 |

FOREIGN PATENT DOCUMENTS

| | | |
|---|---|---|
| WO | 2006110859 A2 | 10/2006 |
| WO | 2008002839 A2 | 1/2008 |
| WO | 2011091369 A1 | 7/2011 |
| WO | 2013116689 A1 | 8/2013 |
| WO | 2013160861 A1 | 10/2013 |

OTHER PUBLICATIONS

Williem, W., Ramesh Raskar, and In Kyu Park. "Depth map estimation and colorization of anaglyph images using local color prior and reverse intensity distribution." Proceedings of the IEEE International Conference on Computer Vision. 2015. (Year: 2015).*
Liew, Y.M. et al. In vivo assessment of human burn scars through automated quantification of vascularity using optical coherence tomography. J Biomed Opt. Jun. 2013;18(6):061213.
Blatter, C. et al. Structural and functional imaging with extended focus dark-field OCT at 1300nm. Proc. SPIE 7889, Optical Coherence Tomography and Coherence Domain Optical Methods in Biomedicine XV (Feb. 11, 2011):1-6.
Enfield, J. et al. In vivo imaging of the microcirculation of the volar forearm using correlation mapping optical coherence tomography (cmOCT). Biomed Opt Express. May 1, 2011; 2(5): 1184-1193.
Great Britain Intellectual Property Office Search Report for GB1503196.6 dated Aug. 28, 2015.
PCT International Search Report for PCT/GB2016/050395 dated Jul. 5, 2016.

* cited by examiner

PROCESSING OPTICAL COHERENCE TOMOGRAPHY SCANS

CROSS-REFERENCE TO RELATED APPLICATIONS

This application is the U.S. national phase entry under 35 U.S.C. § 371 of International Application No. PCT/GB2016/050395, filed Feb. 17, 2016, entitled PROCESSING OPTICAL COHERENCE TOMOGRAPHY SCANS, which in turn claims priority to and benefit of Great Britain Patent Application No. 1503196,6, filed Feb. 26, 2015, the contents of which are incorporated herein by reference in their entirety for all purposes, This invention relates to a method of processing optical coherence tomography (OCT) scans, and associated apparatus.

There is a clinical need for rapid assessment of the depth of partial thickness burns. Superficial burns are easy to clinically diagnose by eye and to treat with salves and dressings. Deep burns are also easy to clinically diagnose by eye and to treat with surgical excision and skin grafts. However, partial thickness burns in which the burn has penetrated partly into the dermis, are difficult to assess by eye, commonly resulting either in unnecessary excision and skin grafts of shallow burns (over treatment), or conversely failure of a deeper burn to respond to treatment with salves etc. causing expensive delays before the deep burn is properly treated with a skin graft.

To address this problem, various methods have been proposed to measure burn depth non-invasively. One such method is Laser Doppler Imaging (LDI) such as is marketed by Moor Instrument (http://gb.moor.co.uk/) of Axminster, Devon, which detects the presence or absence of blood flow in the skin by directing a laser beam at the skin, collecting the reflected light and utilizing the Doppler effect to detect the motion of the blood. However this technique is slow and not very accurate and has not been widely adopted by physicians.

Some researchers have examined the possibility of using Optical Coherence Tomography (OCT) for assessing burns. OCT is a high resolution imaging technology that provides depth-resolved sub-surface images of epithelial tissues including skin.

Most studies have disclosed methods in which burn depth is derived from Polarization-Sensitive OCT (PS-OCT) images (see, for example, Burns. 2004 September; 30(6): 511-7. "Collagen denaturation can be quantified in burned human skin using polarization-sensitive optical coherence tomography"; J Biomed Opt. 2004 January-February; 9(1): 207-12. "Determination of burn depth by polarization-sensitive optical coherence tomography." Srinivas S M1, de Boer J F, Park H, Keikhanzadeh K, Huang H E, Zhang J, Jung W Q, Chen Z, Nelson J S; J Biomed Opt. 2001 October; 6(4):474-9. "In vivo burn depth determination by high-speed fiber-based polarization sensitive optical coherence tomography." Park B H1, Saxer C, Srinivas S M, Nelson J S, de Boer J F; J Biomed Opt. 2012 June; 17(6):066012. doi: 10.1117/1.JBO.17.6.066012. "In vivo imaging of human burn injuries with polarization-sensitive optical coherence tomography", Kim K H1, Pierce M C, Maguluri G, Park B H, Yoon S J, Lydon M, Sheridan R, de Boer J F).

In such a system, the OCT system obtains OCT images that are polarized in one or both orthogonal planes. The theory is that collagen, which is a key component of skin tissue and is strongly birefringent, is damaged or 'denatured' by a burn resulting in loss of birefringence that can be measured from the PS-OCT images. In practice, it is difficult to make PS-OCT systems because the polarization-sensitive optics is expensive and difficult to set up and maintain, so no such device has been commercialised.

Recently, a technique known as speckle-decorrelation OCT (SD-OCT) has been proposed as a method of imaging the blood vasculature in skin (see for example. "Improved microcirculation imaging of human skin in vivo using optical microangiography with a correlation mapping mask." Choi W J, Reif R, Yousefi S, Wang R K. J Biomed Opt. 2014 March; 19(3):36010. doi: 10.1117/1.JBO.19.3.036010.) This technique produces a depth-resolved map or image of blood vessels in skin, and it has already attracted attention as a potential method of assessing burns and burn scars (see for example, "In vivo assessment of human burn scars through automated quantification of vascularity using optical coherence tomography." Liew Y M, McLaughlin R A, Gong P, Wood F M, Sampson D D. J Biomed Opt. 2013 June; 18(6):061213. doi: 10.1117/1.JBO.18.6.061213.)

This technique involves processing of OCT data to detect regions of the OCT images which change with time. Where there is blood flowing within the tissue, the change in the optical pathway for the light flowing through the blood results in a local change in the speckle pattern which is present in all OCT images. This change can be detected by methods such as calculating the decorrelation of a local subset of pixels in OCT signal intensity in the region of interest from image to image, or by calculating the statistical variance of intensity in the region of interest from image to image. All such methods seek to detect changes in the OCT images with time. It is possible to use SD-OCT and similar processing methods to obtain depth-resolved images showing vascular structures in the dermis, by displaying or highlighting the regions of the OCT images where there is change, since these regions are confined to the blood vessels, where blood is flowing and which causes changes in optical pathway.

However, it is desirable that a practical device for use in a clinical setting does not rely on the operator's interpretation of the images. It is desirable that the device produces and displays an indication indicating burn depth in real time, as the OCT probe is moved from place to place on the burn.

According to a first aspect of the invention, there is provided a method of processing optical coherence tomography (OCT) scans through a subject's skin, the method comprising:

receiving a plurality of scans through the subject's skin, the scans representing an OCT signal in slices through the user's skin at different times;

comparing the scans to determine time-varying regions in the scans;

determining a depth-distribution of the time-varying regions.

As such, we have appreciated that the time-varying regions correspond to blood vessels, and the distribution of the blood vessels can be used to determine the extent of burns or other areas of interest.

The determination of the time varying regions may include the determination of a time-varying region dependent upon a magnitude of a difference in an OCT signal between the scans that are compared. Typically, a region will be determined as time-varying if the magnitude of the difference is more than a difference threshold;

typically, where the scans are formed of a plurality of pixels, the sum of the absolute difference in intensity of the pixels in the region is more than the difference threshold.

Alternatively, the determination of the time-varying regions may make use of any of speckle-variance OCT, decorrelation, differencing of phase or any other suitable computational technique which produces a quantitative measure of the difference in the OCT signal in a region, between scans captured at two different times. The method may comprise binning the difference in intensity into discrete ranges, and only considering some of the ranges when determining whether a region is time-varying; typically, ranges which are higher in difference in intensity may be considered with lower ranges being discarded. This has been found to reduce the effects of noise.

The determination of the distribution of the time-varying regions may comprise determining a depth distribution of the time-varying regions through the subject's skin, typically by determining a density of the time-varying regions in the scans. The method may comprise displaying the distribution to an operator, typically as a graph of density of time-varying regions against depth.

As such, the determination of the distribution of the time-varying regions may comprise the determination of a threshold depth through the user's skin at which the depth distribution exceeds a density threshold. As such, this can report to an operator the depth at which the density of time-varying regions, corresponding to blood vessels, increases above a threshold. This threshold depth can therefore be an estimate of the depth of damaged tissue into the skin. The threshold depth can be compared to a predetermined value, and an indication given to an operator whether the threshold depth is larger or smaller than the predetermined value. For example, a buzzer could sound if the threshold depth is larger than the predetermined value, indicating particular deep and so severe burns.

The skin surface is not perfectly flat, but has wrinkles and bumps, and the action of the probe in touching the skin may cause it to deform, potentially resulting in an inaccurate depth distribution of the time-varying regions. Therefore, the method may comprise the determination of a position of the skin's surface in the scans, and determining depth as the distance below the surface. Alternatively, the depth can be determined relative to a fixed datum in the scans, the datum being that given by a stand-off that spaces an OCT probe capturing the OCT signal from the user's skin.

The method may comprise the capturing of a plurality of calibration scans from an area of the user's skin known to be undamaged but typically of similar character, (for example from the laterally opposite side of the subject's body to the burn), the scans representing an OCT signal in slices through the user's skin at different times, comparing the calibration scans to determine time-varying regions in the scan, and determining a depth-distribution of the area of the calibration scans that are occupied by time-varying regions. As such, this can be used to form a comparator for "normal" skin. The distribution of time-varying regions in the calibration scans can be used to determine the density threshold and/or the predetermined value. Alternatively, the density threshold and/or the predetermined value could be determined upon the age and gender of the subject.

Typically, the comparison of the scans and the determination of the distribution of the time-varying regions will be carried out using a processing device, such as a suitably programmed microprocessor.

The slices will typically be approximately or generally perpendicular to the surface of the skin; thus, the scans may be B-scans.

The step of receiving the scans may comprise capturing the scans using an OCT apparatus. The microprocessor may be a microprocessor of the OCT apparatus, or may be a microprocessor separate from the OCT apparatus, for example in a stand-alone computer.

According to a second aspect of the invention, there is provided an optical coherence tomography (OCT) image processing apparatus, comprising a processor, a display coupled to the processor and storage coupled to the processor, the storage carrying program instructions which, when executed on the processor, cause it to carry out the method of the first aspect of the invention.

The image processing apparatus may comprise an OCT apparatus by means of which the OCT scans are captured. As such, the image processing apparatus may comprise an OCT probe arranged to generated interferograms, and the processor may be arranged to generate the images from the interferograms. As such, the image processor may be arranged to process the images as they are captured.

Alternatively, the image processing apparatus may be separate from any OCT apparatus and may be arranged to process the images subsequent to their capture. As such the image processing apparatus may comprise data reception means (such as a network connection or media drive) arranged to receive the images for processing.

There now follows, by way of example only, description of an embodiment of the invention, described with reference to the accompanying drawings, in which.

Figure 1:
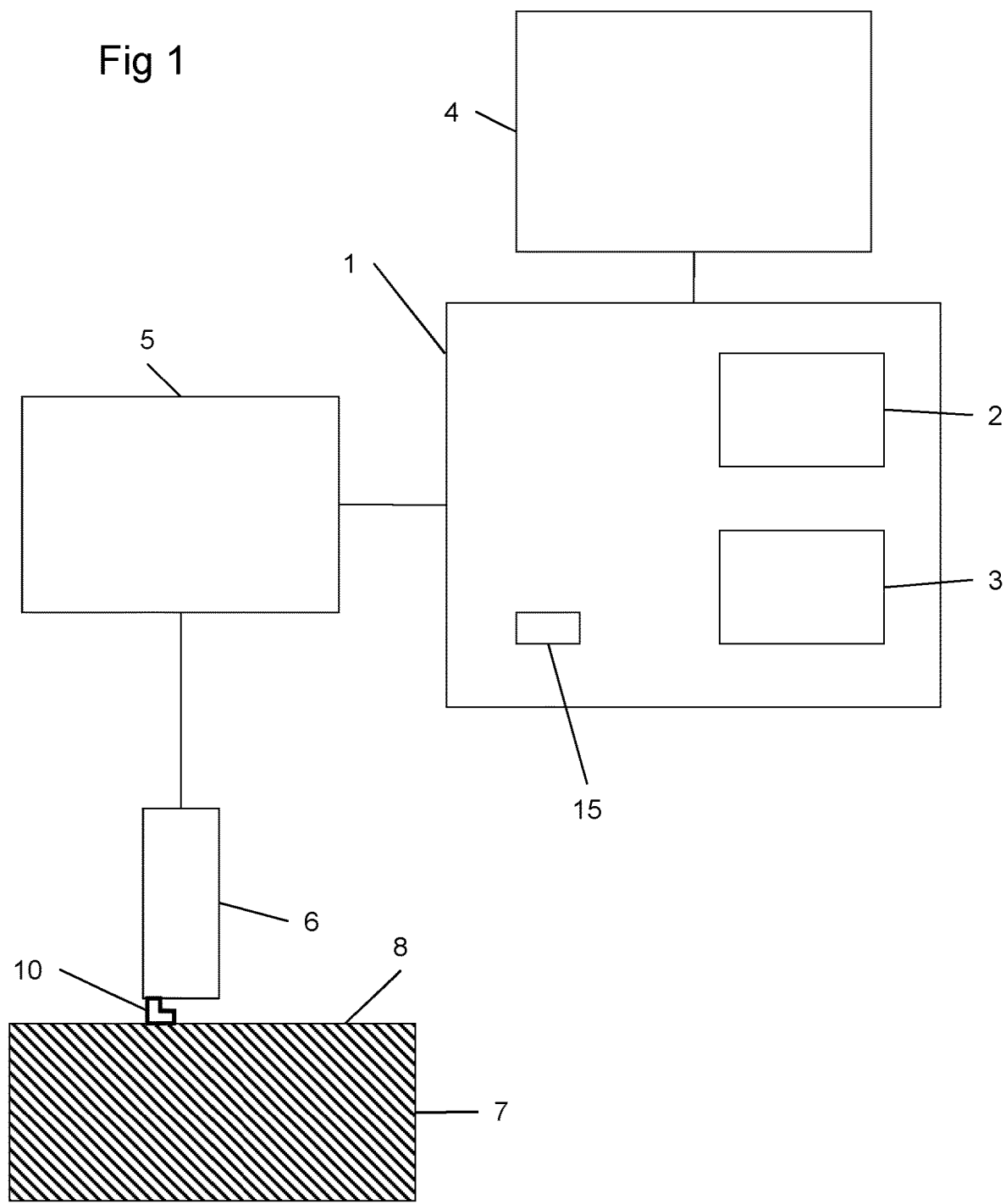
FIG. 1 shows schematically an optical coherence tomography (OCT) apparatus in accordance with an embodiment of the invention.

An optical coherence tomography (OCT) apparatus in accordance with an embodiment of the invention is shown in FIG. 1 of the accompanying drawings. This comprises a computer 1, having a processor 2 and storage 3 (such as a mass storage device or random access memory) coupled to the processor 2. The storage 3 contains data and processor instructions which cause the processor 2 to act as is described below. The computer 1 can be any suitable model; typically a personal computer running an operating system such as Microsoft® Windows® or Apple® Mac OS X® can be used. The computer 1 is also provided with a display 4 controlled by the processor 2 on which any desired graphics can be displayed, and a sound output device 15 such as a buzzer which can sound an alert noise.

The apparatus further comprises an OCT interferometer 5 and associated probe 6. The interferometer 5 interferes light reflected from sample 7 (here, a subject's skin) through probe 6 with light passed along a reference path to generate interferograms. These are detected in the interferometer 5; the measured signal is then passed to the computer 1 for processing. Example embodiments of suitable OCT apparatus can be found in the PCT patent application published as WO2006/054116 or in the VivoSight® apparatus available from Michelson Diagnostics of Orpington, Kent, United Kingdom. A stand-off 10 can be provided which spaces the probe 6 from the user's skin 7.

Such OCT apparatus typically generate multiple B-scans: that is, scans taken perpendicularly through the skin 7. The result of analysis of each interferogram is a bitmap in which the width of the image corresponds to a direction generally parallel to the skin surface and the height corresponds to the depth from the sensor into the skin.

The OCT apparatus takes multiple scans spaced apart in time. Successive images from the same location on a subject's skin can be used to determine the presence of blood flow through blood vessels, by determining areas that have changed between successive images. Such changes can indicate the flow of blood cells through blood vessels. Our preferred technique is speckle decorrelation OCT as described in "In vivo imaging of the microcirculation of the volar forearm using correlation mapping optical coherence tomography (cmOCT)", J Enfield, E Jonathan and M Leahy, Biomed Opt Express. May 1, 2011; 2(5): 1184-1193, but we can also use speckle variance, differencing of intensity or phase, or any other computational technique.

The time interval between the different times should be carefully selected. If the time interval is too short, then there is not enough time for blood to move through the region to make a detectable change. If the time interval is too long, then gross movements of the probe relative to the skin make it difficult or impossible to ensure that the region in the second image is exactly the same location as the region in the first image, and this results in noise in the image. In human skin, a time interval of 3.5 milliseconds works well.

Figures 2, 3:
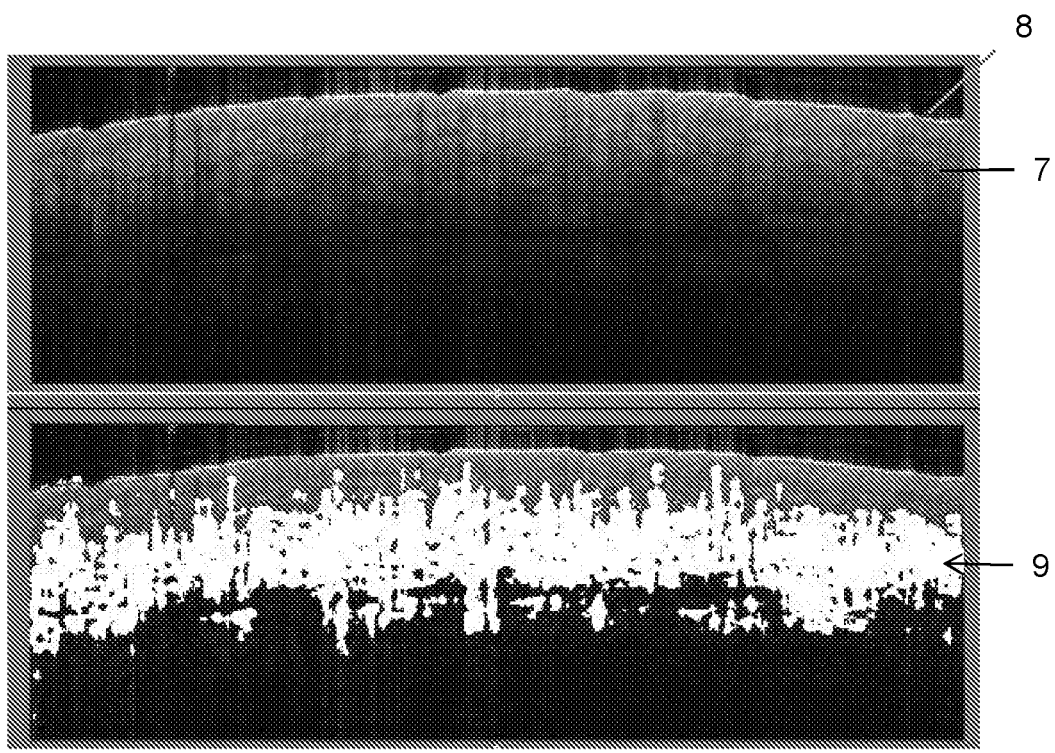
FIG. 2 shows an OCT scan of healthy tissue.
FIG. 3 shows the areas of movement in the OCT scan of FIG. 2.

An example OCT scan is shown at FIG. 2, which shows a user's skin 7, which has a surface 8. The results of comparing this to a successive image in healthy tissue are shown in FIG. 3, where areas of large differences are shown as white as indicated generally at 9. These areas represent areas where there are blood vessels.

Typically, any area where change is determined at above a given threshold is determined to be a changing area. However, in order to reduce the effects of noise, the change levels can collected into ranges—binning in the statistical sense—and then only those ranges of interest being considered. As such, noise tends to be prevalent in the low levels of change, and so the ranges relating to relatively low levels of change may be discarded.

Figure 4:
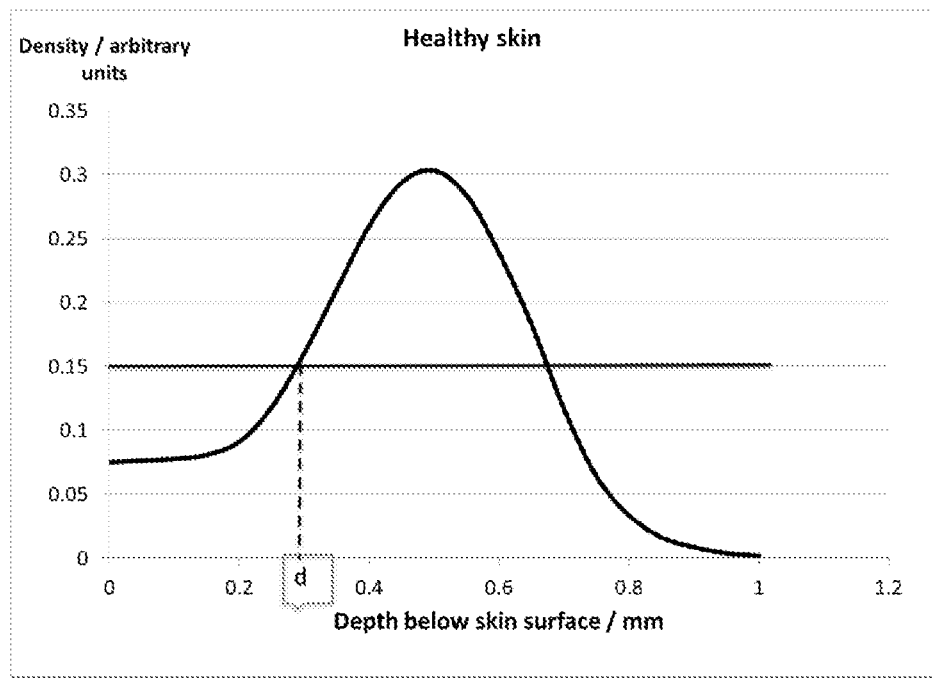
FIG. 4 shows an exemplary graph of density of varying areas with depth through healthy skin.

It is known that healthy skin comprises the epidermis, which does not contain blood vessels, and below it the dermis, which contains blood vessels of sharply increasing density with depth ("Blood Vessels and Lymphatics in Organ Systems", David I Abramson, Academic Press (28. Jan. 1984), ISBN-10: 0124121586, pp 595-32) corresponding to the transition from the 'papillary dermis' to the 'reticular dermis'. The depth distribution of time-varying regions shows an increase at this depth below the skin surface, within the dermis (as shown in FIG. 4 of the accompanying drawings for healthy skin), and then a decrease at still greater depth in the dermis due to the attenuation in the underlying OCT signal strength from optical scattering. However, in skin that has been damaged by a burn, a portion of the blood vessels are damaged or 'cauterised' and can no longer transfer blood. Therefore, the depth distribution of time-varying regions in burn-damaged skin shows a different shape, which may resemble FIG. 5 of the accompanying drawings which shows a greater depth at which the density of time-varying regions increases.

By calculating the density of such time-varying areas in the skin, a measure can be taken of how damaged the skin is by, for example, burns. Burns generally disrupt the blood vessels that are close to the surface; the depth of this disruption can therefore be used to determine how deep a burn extends below the skin without invasive sampling. The depth of a burn is an indication of how serious a burn is, and so can be used in the investigations of a doctor or other health professional as a tool in forming their diagnosis of the burn and determining how to treat it.

As such, the processor 2 is arranged to determine the profile of the density of the changing areas 9. This profile is determined against the depth of the skin. The depth can be determined by defining the zero depth point at a given point in the image (representative of the position of the surface of the standoff 10 which contacts the skin 7), or by determining the position of the skin surface as explained in our earlier PCT patent application published as WO2015/001317.

Figure 5:
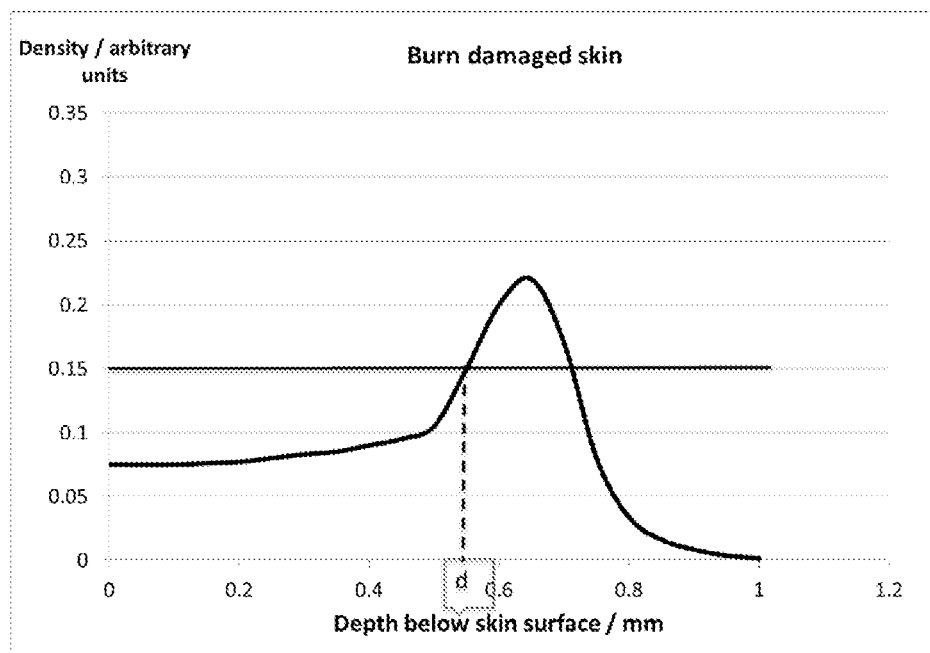
FIG. 5 shows a similar graph to that of FIG. 5 for burnt skin.

This results in a density profile as shown in FIGS. 4 and 5 of the accompanying drawings; this is shown for normal skin in FIG. 4 and burnt skin in FIG. 5. As such, for the burn it is clear that near the surface of the skin there are significantly fewer blood vessels than in normal skin. This curve could be displayed on the display directly to the operator.

However, in the preferred embodiment, by measuring some normal skin in an equivalent area to that which has been (or which is suspected to be) burnt—for example on the opposite lateral side of the body—the processor 2 can determine a threshold depth 13 below which there is a predetermined blood vessel density corresponding to healthy reticular dermis. Alternatively, the threshold could be set based on age, gender and body part and a look-up table filled with measurements of thresholds made of normal skin of subjects with these characteristics and scans locations.

As such, it can then also determine, for suspect burn areas, the skin depth where the blood vessel density rises above the threshold (shown at d in FIG. 4). This is useful information for a doctor or other health professional, as it tells them how deep the burn is, without having to carry out much analysis of the scans themselves. Therefore, the processor 2 can cause this number to be output on the display 4.

Alternatively, or additionally, the processor can be arranged to sound the buzzer 15 should the depth d rise above a predetermined limit, which can be determined from the normal skin scan or again from the age, gender and body part of the subject. If the buzzer sounds, the operator can be clear that there is a burn of some seriousness present. Alternatively, such indication could be given textually on the display, or as a colour depiction (green for normal, red for serious, for example).

The invention claimed is:

1. A method of processing optical coherence tomography (OCT) scans through a subject's skin, the method comprising:
receiving a plurality of scans through the subject's skin, the scans representing an OCT signal in slices through the user's skin at different times;
comparing the scans to determine time-varying regions in the scans; and
determining a distribution of density of the time varying regions with varying depth in the scans;
determination of the time-varying regions comprising a determination of a threshold depth through the user's skin at which a density of the time-varying regions exceeds a density threshold.

2. The method of claim 1, in which the determination of the time varying regions includes the determination of a time-varying region dependent upon a magnitude of a difference in an OCT signal between the scans that are compared.

3. The method of claim 1 in which the determination of the time-varying regions makes use of any of speckle-variance OCT, decorrelation, or differencing of intensity or phase.

4. The method of claim 1, comprising displaying the distribution to an operator, as a graph of density of time-varying regions against depth.

5. The method of claim 1, comprising comparing the threshold depth to a predetermined value, and giving an indication to an operator whether the threshold depth is larger or smaller than the predetermined value.

6. The method of claim 5, in which the predetermined value is obtained from a look-up table containing values corresponding to characteristics of the subject's skin.

7. The method of claim 6, in which the look-up table values correspond to the location of the scan on the body, the age and the gender of the subject.

8. The method of claim 1, comprising the capturing of a plurality of calibration scans from an area of the user's skin known to be undamaged, the scans representing an OCT signal in slices through the user's skin at different times, comparing the calibration scans to determine time-varying regions in the scan, and determining a depth-distribution of the calibration scans that are occupied by time-varying regions.

9. The method of claim 8, in which the depth distribution of time-varying regions in the calibration scans is used to determine the density threshold and/or the predetermined value.

10. The method of claim 1, in which the comparison of the scans and the determination of the distribution of the time-varying regions is carried out using a processing device, such as a suitably programmed microprocessor.

11. The method of claim 1, in which the step of receiving the scans comprises capturing the scans using an OCT apparatus.

12. An optical coherence tomography (OCT) image processing apparatus, comprising a processor, a display coupled to the processor and storage coupled to the processor, the storage carrying program instructions which, when executed on the processor, cause it to carry out the method of claim 1.

13. The image processing apparatus of claim 12, comprising an OCT apparatus by means of which the OCT scans are captured.

14. The method of claim 1, wherein the density threshold being obtained by:
capturing a plurality of calibration scans from an area of the subject's skin known to be undamaged;
determining time varying regions from the plurality of calibration scans; and
determining a depth distribution of an area of the calibration scans occupied by the time varying regions.

15. The method of claim 1 wherein comparing the scans to determine time-varying regions in the scans comprises one of calculating a decorrelation of a local subset of pixels in OCT signal intensity in a region of interest from image to image, or calculating a statistical variance of intensity in the region of interest from image to image, or calculating difference in phase in the region of interest from image to image.

16. The method of claim 1 further comprising:
determining a position of skin's surface in the scans; and
determining depth as a distance below the position of the skin's surface.

17. The method of claim 1 further comprising displaying the distribution of density as a graph of density of time-varying regions against depth.

* * * * *